United States Patent
Tadayyon et al.

(10) Patent No.: US 11,049,238 B2
(45) Date of Patent: Jun. 29, 2021

(54) SYSTEMS AND METHODS FOR PREDICTION OF TUMOR RESPONSE TO CHEMOTHERAPY USING PRE-TREATMENT QUANTITATIVE ULTRASOUND PARAMETERS

(71) Applicant: Sunnybrook Research Institute, Toronto (CA)

(72) Inventors: Hadi Tadayyon, North York (CA); Gregory J. Czarnota, Oakville (CA); Ali Sadeghi-Naini, North York (CA); Mehrdad Gangeh, Toronto (CA); Lakshmanan Sannachi, Toronto (CA); William Tyler Tran, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 481 days.

(21) Appl. No.: 15/739,003

(22) PCT Filed: Jun. 21, 2016

(86) PCT No.: PCT/CA2016/050727
§ 371 (c)(1),
(2) Date: Dec. 21, 2017

(87) PCT Pub. No.: WO2016/205936
PCT Pub. Date: Dec. 29, 2016

(65) Prior Publication Data
US 2018/0189947 A1   Jul. 5, 2018

Related U.S. Application Data

(60) Provisional application No. 62/182,773, filed on Jun. 22, 2015.

(51) Int. Cl.
*G06T 7/00* (2017.01)
*A61B 8/08* (2006.01)
(Continued)

(52) U.S. Cl.
CPC ............ *G06T 7/0012* (2013.01); *A61B 8/085* (2013.01); *A61B 8/0825* (2013.01); *A61B 8/14* (2013.01);
(Continued)

(58) Field of Classification Search
CPC .............................. G06T 7/0012; G16H 50/20
See application file for complete search history.

(56) References Cited

U.S. PATENT DOCUMENTS 6,154,560 A    11/2000  Cothren
10,580,517 B2 *  3/2020  Bagaev .................. G16H 50/30
(Continued)

FOREIGN PATENT DOCUMENTS

| WO | 2014061258 | 4/2014 |
| WO | 2014113786 | 7/2014 |
| WO | 2014186899 | 11/2014 |

OTHER PUBLICATIONS

Batsis, C. et al. "Neoadjuvant chemotherapy for breast cancer: does pretreatment axillary nodal staging improve decision making?." Annals of surgical oncology 16.4 (2009): 1063-1064.
(Continued)

*Primary Examiner* — Santiago Garcia
(74) *Attorney, Agent, or Firm* — Quarles & Brady LLP

(57) ABSTRACT

Systems and methods for using quantitative ultrasound ("QUS") techniques to generate imaging biomarkers that can be used to assess a prediction of tumor response to different chemotherapy treatment regimens are provided. For instance, the imaging biomarkers can be used to subtype tumors that have resistance to certain chemotherapy regimens prior to drug exposure. These imaging biomarkers can therefore be useful for predicting tumor response and for assessing the prognostic value of particular treatment regimens.

23 Claims, 5 Drawing Sheets

(51) Int. Cl.
  *G16H 50/20* (2018.01)
  *G16H 20/10* (2018.01)
  *A61B 8/14* (2006.01)
  *A61B 8/00* (2006.01)
  *G06K 9/62* (2006.01)
  *A61B 5/00* (2006.01)

(52) U.S. Cl.
  CPC ............ *A61B 8/5215* (2013.01); *A61B 8/587* (2013.01); *G06K 9/6277* (2013.01); *G16H 20/10* (2018.01); *G16H 50/20* (2018.01); *A61B 5/4848* (2013.01); *G06K 9/6269* (2013.01); *G06K 9/6276* (2013.01); *G06T 2207/10132* (2013.01); *G06T 2207/20076* (2013.01); *G06T 2207/30096* (2013.01)

(56) References Cited

U.S. PATENT DOCUMENTS

| | | | |
|---|---|---|---|
| 2005/0215883 A1 | 9/2005 | Hundley | |
| 2006/0002631 A1* | 1/2006 | Fu | G06K 9/3233 382/294 |
| 2007/0117133 A1* | 5/2007 | Trieu | A61K 31/337 435/6.12 |
| 2007/0286342 A1* | 12/2007 | Fuller | A61N 5/103 378/65 |
| 2009/0069196 A1* | 3/2009 | Gehrmann | C12Q 1/6886 506/16 |
| 2009/0239223 A1* | 9/2009 | Gehrmann | C12Q 1/6886 435/5 |
| 2010/0317001 A1* | 12/2010 | Parissenti | C12Q 1/6886 435/5 |
| 2011/0026798 A1 | 2/2011 | Madabhushi | |
| 2013/0094743 A1* | 4/2013 | Coenegrachts | G06T 7/0016 382/131 |
| 2014/0010427 A1* | 1/2014 | Kriston | A61B 6/12 382/131 |
| 2014/0228241 A1* | 8/2014 | Gehrmann | C12Q 1/6886 506/9 |
| 2015/0297172 A1 | 10/2015 | Takagi | |
| 2015/0376714 A1* | 12/2015 | Brase | C12Q 1/6886 506/9 |
| 2016/0007944 A1* | 1/2016 | O'Connor | A61B 6/037 600/431 |
| 2016/0120437 A1* | 5/2016 | Graham | A61B 5/055 600/411 |
| 2019/0019300 A1* | 1/2019 | Simpson | G06T 7/45 |

OTHER PUBLICATIONS

European Patent Office, Extended European Search Report for 16813431, dated Feb. 5, 2019, 11 pages.

Giordano Sh. Update on locally advanced breast cancer. 'The Oncol. Jan. 2003;8(6):521-30.

International Searching Authority, International Search Report & Written Opinion for PCT/CA2016/050727, dated Oct. 6, 2016, 8 pages.

Mamounas, E. P. "Combined Use of Clinical and Pathologic Staging Variables to Define Outcomes for Breast Cancer Patients Treated With Neoadjuvant Therapy" Breast Diseases: a YB Quarterly 19.4 (2009): 358-359.

Sadeghi-Naini A, et al. Quantitative ultrasound evaluation of tumor cell death response in locally advanced breast cancer patients receiving chemotherapy. Clin Cancer Res. Apr. 15, 2013;19(8):2163-74.

Sannachi, L., et al. "Non-invasive evaluation of breast cancer response to chemotherapy using quantitative ultrasonic backscatter parameters." Medical image analysis 20.1 (2015): 224-236.

Tadayyon, H., et al. "Quantification of ultrasonic scattering properties of in vivo tumor cell death in mouse models of breast cancer." Translational oncology 8.6 (2015): 463-473.

The American Society of Breast Surgeons. Position Statement on breast cancer lumpectomy margins. Am Soc breast Surg. 2013;(1):25-31.

* cited by examiner

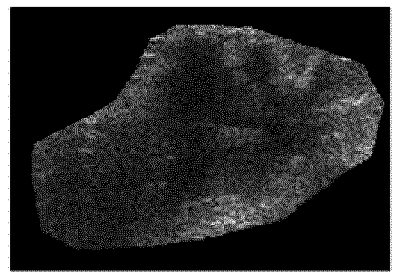
FIG. 3A
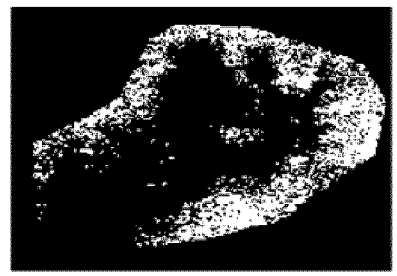
FIG. 3B
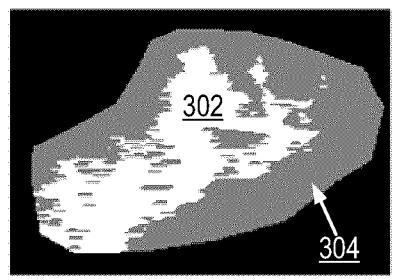
FIG. 3C
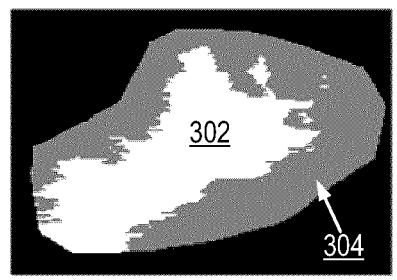
FIG. 3D
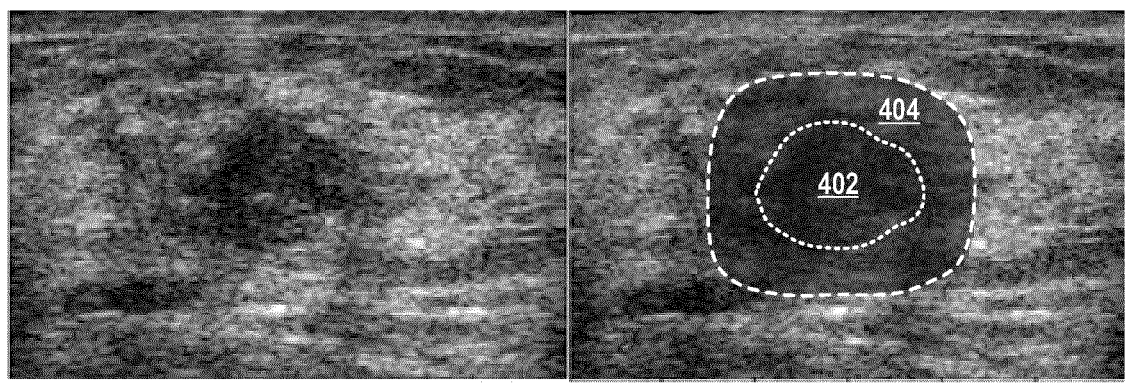
FIG. 4A
FIG. 4B

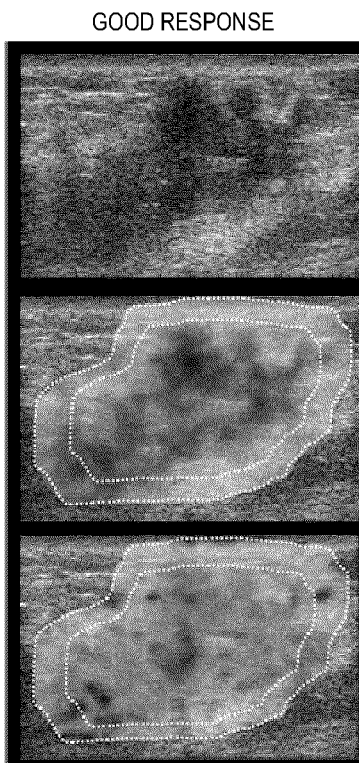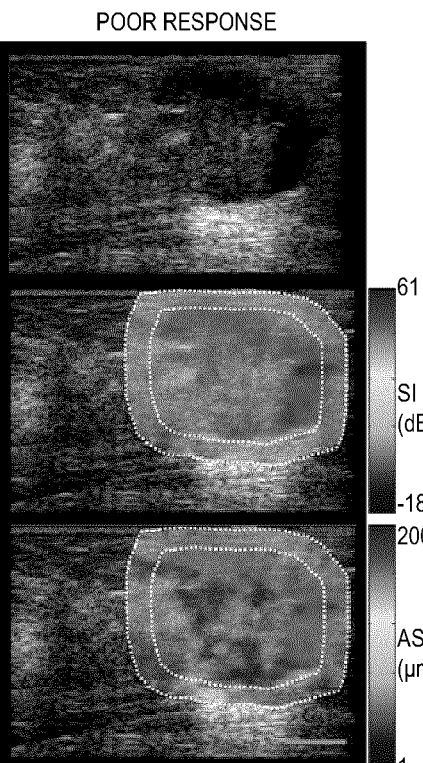
FIG. 5A  FIG. 5B  FIG. 5C  FIG. 5E  FIG. 5F  FIG. 5G
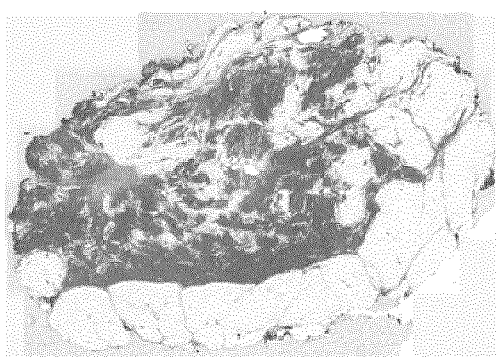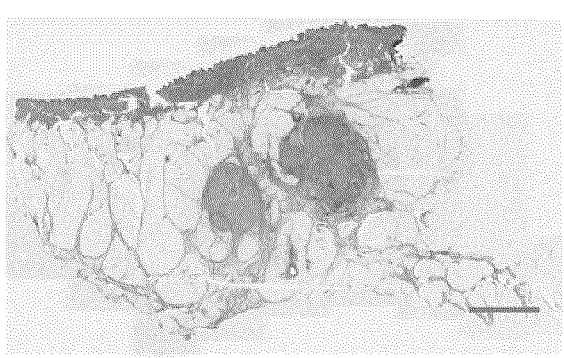
FIG. 5D  FIG. 5H

SYSTEMS AND METHODS FOR PREDICTION OF TUMOR RESPONSE TO CHEMOTHERAPY USING PRE-TREATMENT QUANTITATIVE ULTRASOUND PARAMETERS

CROSS-REFERENCE TO RELATED APPLICATIONS

This application represents the national stage entry of PCT International Application PCT/CA2016/050727 filed Jun. 21, 2016, which claims the benefit of U.S. Provisional Application 62/182,773 filed Jun. 22, 2015. The contents of this application are hereby incorporated by reference as if set forth in their entirety herein.

BACKGROUND OF THE INVENTION

The field of the invention is systems and methods for quantitative ultrasound ("QUS"). More particularly, the invention relates to systems and methods for using quantitative ultrasound to generate imaging biomarkers from which tumors can be classified based on a prediction of the tumor's response to different treatment regimens.

QUS techniques examine the frequency-dependent backscatter of tissues independent of the instrument settings. Based on data acquired using these techniques, quantitative parameters including mid-band fit ("MBF"), spectral slope ("SS"), spectral 0-Mhz intercept ("SI"), spacing among scatterers ("SAS"), attenuation coefficient estimate ("ACE"), average scatterer diameter ("ASD"), and average acoustic concentration ("AAC") can be computed.

There is a current desire for the discovery of imaging biomarkers that allow early prediction of tumor response to therapy.

SUMMARY OF THE INVENTION

The present invention overcomes the aforementioned drawbacks by providing a computer-implemented method for assessing a prediction of tumor response to a chemotherapy treatment using an ultrasound system. Ultrasound echo signal data are acquired from a subject using the ultrasound system. An anatomical image of the subject is provided, and a region-of-interest (ROI) that contains a tumor is identified in the anatomical image. At least one parametric map is generated from the ultrasound echo signal data. The at least one parametric map has pixel values associated with a parameter computed from the acquired ultrasound echo signal data acquired from the ROI. At least one of a first-order statistical measure, a second-order statistical measure, or an image quality measure is computed based on the at least one parametric map. The tumor is then classified based on a prediction of the tumor's response to a chemotherapy treatment by applying a classifier to the computed at least one first-order statistical measure, second-order statistical measure, or image quality measure.

It is another aspect of the invention to provide a computer-implemented method for using an ultrasound system to assess a prognosis for a subject who will be treated with a particular tumor treatment regimen. Ultrasound echo signal data are acquired from a subject using the ultrasound system. An anatomical image of the subject is provided, and a region-of-interest (ROI) that contains a tumor is identified in the anatomical image. At least one parametric map is generated from the ultrasound echo signal data. The at least one parametric map has pixel values associated with a parameter computed from the acquired ultrasound echo signal data acquired from the ROI. At least one of a first-order statistical measure, a second-order statistical measure, or an image quality measure is computed based on the at least one parametric map. The tumor is then classified based on a prognosis for the subject following treatment with a particular tumor treatment regimen. The tumor is classified in this manner by applying a classifier to the computed at least one first-order statistical measure, second-order statistical measure, or image quality measure. As an example, the prognosis for the subject can be based on an estimator, which may include a progression-free survival, a survival rate, and a survival time.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 3A-3D depict an example process of segmenting an image of a tumor into a region-of-interest ("ROI") corresponding to the tumor core and an ROI corresponding to a margin around the tumor core.

FIGS. 4A-4B depict a representative B-mode image (FIG. 4A) and corresponding tumor core and tumor margin ROIs (FIG. 4B).

FIGS. 5A-5H illustrate comparisons of a responding and a non-responding patient's tumor. Shown are original B-mode images (FIGS. 5A and 5E); SI parametric images (FIGS. 5B and 5F); ASD parametric images (FIGS. 5C and 5G) with core and margin ROIs outlined in white; and H&E-stained post-surgical breast specimen (FIGS. 5D and 5H) with pink indicating normal breast tissue, light pink indicating fibrosis, and purple indicating residual tumor tissue.

DETAILED DESCRIPTION OF THE INVENTION

Described here are systems and methods for using quantitative ultrasound ("QUS") techniques to generate imaging biomarkers that can be used to assess a prediction of tumor response to different chemotherapy treatment regimens. For instance, the imaging biomarkers can be used to subtype tumors that have resistance to certain chemotherapy regimens prior to drug exposure. These imaging biomarkers can therefore be useful for predicting tumor response.

Thus, described here are systems and methods for using a quantitative ultrasound technique to classify tumors, such as locally advanced breast tumors and others, in terms of their chemo-responsiveness prior to beginning neoadjuvant chemotherapy treatment. This technique permits the identification of tumor subtypes that have resistance to certain chemotherapy drugs without the need for exposing the patient to those drugs.

Figure 1:
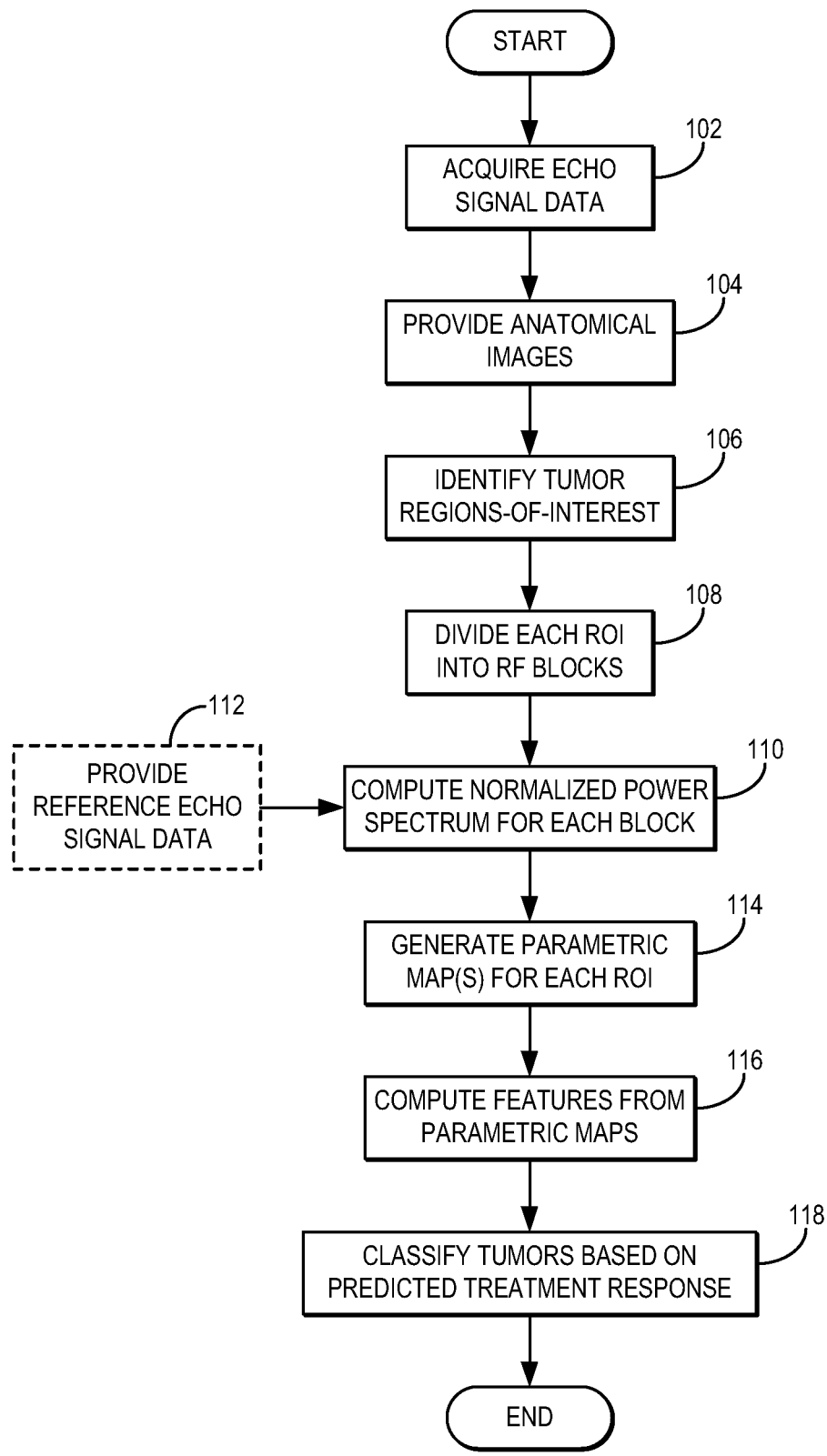
FIG. 1 is a flowchart setting forth the steps of an example method for using quantitative ultrasound to generate imaging biomarkers that can be used to classify a tumor based on a prediction of treatment response.

Referring now to FIG. 1, a flowchart is illustrated as setting forth the steps of an example method for using quantitative ultrasound ("QUS") techniques to generate imaging biomarkers that indicate an efficacy of chemotherapy treatment regimens on a tumor. Raw echo signal data (e.g., ultrasound radio frequency ("RF") data) are acquired from the subject, as indicated at step 102. The raw echo signal data are acquired in response to ultrasound transmitted to the subject. The transmitted ultrasound is preferably conventional-frequency, but can also be high-frequency ultrasound. In some instances, it may also be beneficial to use combinations of low-frequency and high-frequency ultrasound depending on the depth of the tissue and the desired imaging resolution. For instance, higher ultrasound frequencies are capable of increasing imaging resolution, but at the cost of limiting the penetration depth of the ultrasound. For example, ultrasound frequencies in the range of 20-60 MHz can achieve imaging resolutions in the range of 30-80 µm, whereas ultrasound frequencies in the range of 1-20 MHz can achieve imaging resolutions of 30 µm to about 1.5 mm.

By way of example, the raw echo signal data can be acquired from a subject using an ultrasound system operating at a conventional ultrasound frequency, such as 6 MHz or 10 MHz. Alternatively, the ultrasound system can be operated to generate high frequency ultrasound, such as greater than 20 MHz. The echo signals in the ultrasound RF data can be obtained in a number of differently oriented image planes.

Images of the subject that depict the subject's anatomy are also provided, as indicated at step 104. As one example, the images can be B-mode images that are provided by acquiring the images from the subject, or by retrieving previously acquired B-mode images from data storage.

One or more regions-of-interest ("ROIs") are then identified in the provided images of the subject, as indicated at step 106. In general, one or more ROIs are identified for each tumor depicted in the provided images. Preferably, at least two ROIs are identified for each tumor: one ROI being associated with the core of the tumor and one ROI being associated with the tumor margin.

The ROIs are then divided into RF blocks, as indicated at step 108. As one example, each block includes twenty scan lines that are each ten wavelengths long. This example corresponds to blocks that are 2 mm×2 mm assuming a speed of sound of 1540 m/s. As an example, each selected ROI can be divided into RF blocks using a sliding window approach with or without overlap between adjacent windows. Each window is advantageously sized to be larger than the minimum size required to obtain reliable spectral parameters that are independent of window length. For instance, the window can be sized to be at least as large as ten wavelengths of the transmitted ultrasound.

For each RF block, a normalized power spectrum is computed from the acquired raw echo signal data to make the analysis of the raw echo signal data system-independent, as indicated at step 110. By way of example, the raw echo signal data can be normalized on a sliding window basis using reference data obtained from a tissue-mimicking phantom, a planar reflector, or the like. To this end, reference echo signal data can optionally be provided, as indicated at step 112.

For example, a tissue-mimicking phantom composed of agar gel embedded with glass microspheres can be used to obtain reference echo signal data. Preferably, such reference echo signal data can be used for normalizing the mean power spectrum on which linear regression analyses will be performed in order to extract a number of quantitative ultrasound parameters.

As another example, a planar reflector, such as a Plexiglas planar reflector, can be used to obtain reference echo signal data to be used when computing SAS in order to avoid affecting the estimation of SAS in the tissue by the glass scatterers in the tissue-mimicking phantom. Reference echo signal data obtained from such a planar reflector are preferably obtained at a plurality of different depths to cover the potential tissue depths in the region of the subject. As an example, twelve equally spaced depths ranging from 1-6 cm can be utilized.

For a given data window, the corresponding reference window can be selected by nearest neighbor interpolation. Spectral normalization of the mean power spectrum may be performed using RF echoes obtained from a reference phantom, $e_p(t, x_i)$, to remove the system transfer function. The mean normalized power spectrum, S(f), of a window can be written as, $$S(f) = \frac{\sum_{i=N}^{M} |FFT(e_s(t, x_i))|^2}{\sum_{i=N}^{M} |FFT(e_p(t, x_i))|^2}; \quad (1)$$

where f is frequency, t is the time-gated RF echo segment in the window, $x_i$ is the $i^{th}$ lateral position in the window, and FFT( . . . ) is the Fast Fourier Transform operator.

From the normalized power spectra, one or more parametric maps are generated for each ROI, as indicated at step 114. For instance, the parametric maps are images whose pixel values are representative of quantitative ultrasound parameters computed from the raw echo signal data. Examples of such parameters include mid-band fit ("MBF"), spectral slope ("SS"), spectral 0-Mhz intercept ("SI"), spacing among scatterers ("SAS"), attenuation coefficient estimate ("ACE"), average scatterer diameter ("ASD"), and average acoustic concentration ("AAC"). Quantitative ultrasound parameters such as ASD and AAC can be estimated by fitting a theoretical tissue backscatter model to the measured backscatter signal from the tissue of interest. For example, estimated and theoretical backscatter coefficients can be used to compute ESD and EAC.

As one example, a linear regression analysis, such as a least squares fit, can be applied to a normalized power spectrum to extract the MBF, SS, and SI parameters as follows:

$$S(f) = SS \cdot f + SI \quad (2);$$

$$MBF = SS \cdot f_c + SI \quad (3);$$

where $f_c$ is the frequency at the center of the analysis bandwidth, which may be the −6 dB frequency bandwidth. More generally, the bandwidth can be determined empirically, such as from the power spectrum of a reference phantom or planar reflector.

One or more features, such as first-order statistical measures, second-order statistical measures, and image quality measures, are next extracted from the parametric maps, as indicated at step 116. Then, as indicated at step will 118 and as will be described below in more detail, the one or more features are provided to a classifier to subtype the tumor and to provide a statistical estimate indicating whether the tumor is likely to have resistance to certain chemotherapy regimens prior to exposing the tumor to the chemotherapy drugs.

First-order statistics are generally computed from a function that measures the probability of a certain pixel occurring in an image and, therefore, they depend on individual pixel values and not on the interaction of neighboring pixel values. By way of example, the first-order statistical measure may be the mean of intensities in a parametric map. Alternatively, the first-order statistical measure may be the standard deviation, skewness, or kurtosis of a parametric map.

In general, second-order statistics are computed from a probability function that measures the probability of a pair of pixel values occurring at some offset in an image. This probability function is typically referred to as a "co-occurrence matrix" because it measures the probability of two pixel values co-occurring at the given offset. An example of the co-occurrence matrix is the gray level co-occurrence matrix ("GLCM"). These second-order statistics can generally be referred to as textural features of an image. The application of textural analysis on the quantitative ultrasound parametric maps, where instrument dependencies are preferably removed via the aforementioned normalization, provides advantageous information for the classification techniques described later. By way of example, second-order statistical measures may include contrast, energy, homogeneity, or correlation. Alternatively, the second-order statistical measure could include other second-order statistics, including autocorrelation, dissimilarity, GLCM variance, entropy, cluster shade, cluster prominence, and maximum probability.

The GLCM represents, statistically, the angular relationship between neighboring pixels as well as the distance between them. Based on the statistical information provided by a GLCM, several textural features can be defined and extracted.

Contrast ("CON") represents a measure of difference between the lowest and highest intensities in a set of pixels. Energy ("ENE") measures the frequency of occurrence of pixel pairs and quantifies its power as the square of the frequency of gray-level transitions. Homogeneity ("HOM") measures the incidence of pixel pairs of different intensities; thus, as the frequency of pixel pairs with close intensities increases, HOM increases. Correlation ("COR") measures the intensity correlation between pixel pairs.

In some embodiments, to estimate second-order statistical measures the computed parametric maps are processed using a GLCM-based texture analysis process to extract the aforementioned second-order statistical measures, which may also be referred to as textural features. A GLCM is an $N_g \times N_g$ matrix, where $N_g$ is the number of quantized gray levels in the image for which the GLCM is computed (e.g., the parametric maps in this instance). Each element in the GLCM, $p(i,j)$, is a statistical probability value for changes between the $i^{th}$ and $j^{th}$ gray levels at a particular displacement distance, d, and angle, θ. Thus, given $p(i,j)$ as an element in an $N_g \times N_g$ GLCM, the above-mentioned textural parameters can be defined as follows:

$$CON = \sum_{k=0}^{N_g-1} k^2 \left( \sum_{i=1}^{N_g} \sum_{j=1}^{N_g} p(i,j) \right) \text{ with } k = |i-j|; \quad (4)$$

$$ENE = \sum_{i=1}^{N_g} \sum_{j=1}^{N_g} p(i,j)^2; \quad (5)$$

$$HOM = \sum_{i=1}^{N_g} \sum_{j=1}^{N_g} \frac{p(i,j)}{1+|i-j|}; \quad (6)$$

$$COR = \frac{\sum_{i=1}^{N_g} \sum_{j=1}^{N_g} (i-\mu_x)(j-\mu_y) p(i,j)}{\sigma_x \sigma_y}; \quad (7)$$

where $\mu_x$ and $\mu_y$ are the means for the columns and rows, respectively, of the GLCM, $$\mu_x = \sum_{i=1}^{N_g} \sum_{j=1}^{N_g} i \cdot p(i,j); \quad (8)$$

$$\mu_y = \sum_{i=1}^{N_g} \sum_{j=1}^{N_g} j \cdot p(i,j); \quad (9)$$

and where $\sigma_x$ and $\sigma_y$ are the standard deviations for the columns and rows, respectively, of the GLCM, $$\sigma_x^2 = \sum_{i=1}^{N_g} \sum_{j=1}^{N_g} (i-\mu_x)^2 \cdot p(i,j); \quad (10)$$

$$\sigma_y^2 = \sum_{i=1}^{N_g} \sum_{j=1}^{N_g} (j-\mu_y)^2 \cdot p(i,j). \quad (11)$$

A number of different GLCMs can be constructed for each parametric map. For example, sixteen symmetric GLCMs can be constructed considering each pixel's neighbors located at the displacement distances, d, of one to four pixels with angular values, θ, of 0-135 degrees with 45 degree increments. The second-order statistical measures, or textural features, can then be extracted from the corresponding GLCMs of each QUS parametric map and consequently averaged to produce the computed second-order statistical measures.

Image quality measures can include signal-to-noise ratio ("SNR") and contrast-to-noise ratio ("CNR"). As another example, image quality features can be defined to compare pixel intensities between two ROIs, such as an ROI associated with a tumor core and an ROI associated with a tumor margin. Two such image quality features are a core-to-margin ratio ("CMR") and a core-to-margin contrast ratio ("CMCR"), which can be computed as follows:

$$CMR = \frac{\text{mean}(ROI_{core})}{\sigma(ROI_{margin})}; \quad (12)$$

$$CMCR = \frac{|\text{mean}(ROI_{core}) - \text{mean}(ROI_{margin})|}{\frac{1}{2}(\sigma(RIO_{core}) + \sigma(ROI_{margin}))}; \quad (13)$$

where mean ($ROI_{core}$) is the mean image intensity value for a parametric map in the ROI associated with the tumor core, mean ($ROI_{margin}$) is the mean image intensity value for a parametric map in the ROI associated with the tumor margin, $\sigma(ROI_{core})$ is the standard deviation of image intensity values for a parametric map in the ROI associated with the tumor core, and $\sigma(ROI_{margin})$ is the standard deviation of image intensity values for a parametric map in the ROI associated with the tumor margin.

Referring again to FIG. 1, the step of providing the one or more features extracted from the parametric maps to a classifier to subtype the tumor can include using a discriminant analysis, such as a linear discriminant analysis ("LDA"). As one example, a Fisher's linear discriminant ("FLD") classifier can be used. In other embodiments, other classifiers, such as a support vector machine ("SVM") classifier or a k-nearest neighbors ("k-NN") classifier, can be used. In some embodiments, the tumor can be classified based on a prediction of the tumor's response to a chemotherapy treatment. In some other embodiments, the tumor can be classified based on a prognosis for the subject following treatment with a particular tumor treatment regimen.

An FLD-based classifier is a linear classifier that projects multidimensional data onto a feature space that maximizes the ratio of between-class to within-class variance, and performs well when the data can be separated by a line. To classify a tumor to indicate its response to different treatment regimens using LDA (e.g., an FLD-based classifier), the linear discriminant can be trained and tested using, for example, a leave-one-out approach for the tissue being analyzed. Similar training and testing can be performed using other classifiers, such as SVM and k-NN. Examples of tissues that can be analyzed include, but are not limited to, tissues in the breast, liver, brain, prostate, kidney, bladder, gallbladder, spleen, cervix, blood vessels, muscle, and bone. This training can be performed in real-time or, preferably, can be performed off-line with the results stored in a feature set database that can be provided during processing. Such a feature set database includes combinations of the first-order statistical measures, second-order statistical measures, and image quality measures that maximize, or otherwise provide desired levels of, the specificity and sensitivity of the tumor classification. As discussed above, these feature sets can define imaging biomarkers for the tumor and can indicate the tumor response to different treatment regimens before exposing the subject to chemotherapy.

SVM-based classifiers build a model (e.g., from training data) to have the largest possible gap between the classes, and then predict the class association of test data samples based on which side of the gap they fall on. As one example, a Gaussian radial basis function can be used as the kernel function for an SVM-based classifier. In general, the kernel function defines how data samples will be mapped into the new feature space, called kernel space. SVM model parameters can be optimized using a grid search. In a leave-one-out validation scheme, a k-NN classifier can be used to predict the class association of a test point in the feature space based on the class that forms the majority of the points neighboring the point of interest, and based also on the distance between those points and the point of interest. The SVM and k-NN based classifiers are non-linear classifiers, which are advantageous when the classes cannot be separated by a line and when a large number of features is available.

Figure 2:
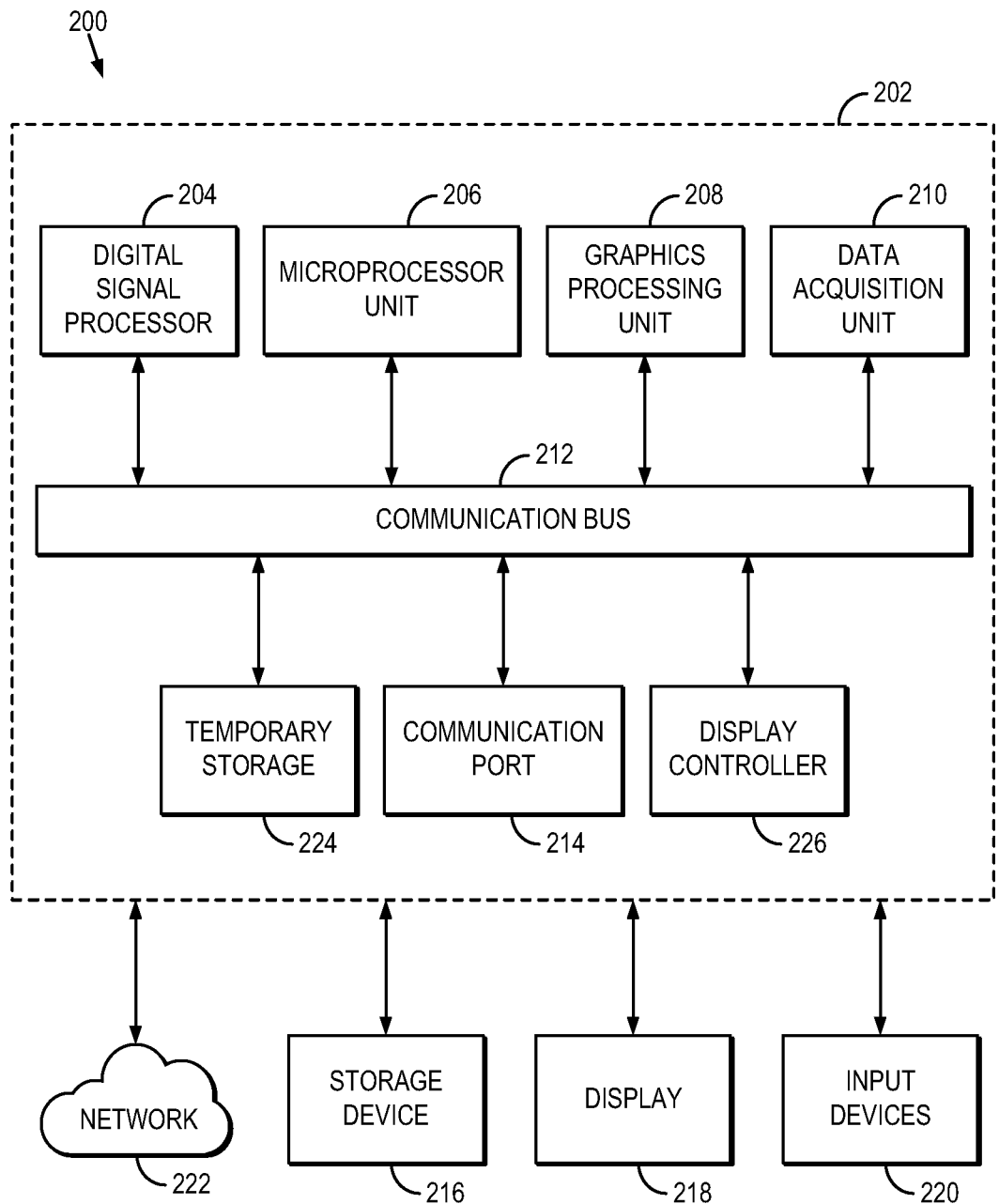
FIG. 2 is an example of a computer system that can implement the methods and algorithms described here.

Referring now to FIG. 2, a block diagram of an example computer system 200 that can be configured to classify tumors based on predicted treatment response using the quantitative ultrasound techniques described above, is illustrated. The echo signal data can be provided to the computer system 200 from an ultrasound system, or from a data storage device, and is received in a processing unit 202.

In some embodiments, the processing unit 202 can include one or more processors. As an example, the processing unit 202 may include one or more of a digital signal processor ("DSP") 204, a microprocessor unit ("MPU") 206, and a graphics processing unit ("GPU") 208. The processing unit 202 can also include a data acquisition unit 210 that is configured to electronically receive data to be processed, which may include echo signal data or digital images. The DSP 204, MPU 206, GPU 208, and data acquisition unit 210 are all coupled to a communication bus 212. As an example, the communication bus 212 can be a group of wires, or a hardwire used for switching data between the peripherals or between any component in the processing unit 202.

The DSP 204 can be configured to receive and processes the echo signal data. For instance, the DSP 204 can be configured to receive the echo signal data and form a digital image therefrom. The MPU 206 and GPU 208 can be configured to process the echo signal data, or a digital image formed therefrom, in conjunction with the DSP 204. As an example, the MPU 206 can be configured to control the operation of components in the processing unit 202 and can include instructions to perform processing of the echo signal data, or a digital image formed therefrom, on the DSP 204. Also as an example, the GPU 208 can process image graphics. Also In some embodiments, the DSP 204 can be configured to process the echo signal data, or a digital image formed therefrom, received by the processing unit 202 in accordance with the algorithms described herein. Thus, the DSP 204 can be configured to generate parametric maps; to compute first-order order statistical measures, second-order statistical measures, and image quality measures of the parametric maps; and to classify tumors based on the first-order order statistical measures, second-order statistical measures, and image quality measures of the parametric maps.

The processing unit 202 preferably includes a communication port 214 in electronic communication with other devices, which may include a storage device 216, a display 218, and one or more input devices 220. Examples of an input device 220 include, but are not limited to, a keyboard, a mouse, and a touch screen through which a user can provide an input.

The storage device 216 is configured to store echo signal data, digital images, or both, whether provided to or processed by the processing unit 202. The display 218 is used to display images, such as images that may be stored in the storage device 216, and other information. Thus, in some embodiments, the storage device 216 and the display 218 can be used for displaying the parametric maps, and for outputting other information such as data plots or other reports based on statistical measures computed from the parametric maps, including information indicating a classification of tumors and predicted treatment response for tumors.

The processing unit 202 can also be in electronic communication with a network 222 to transmit and receive data, including echo data, images, and other information. The communication port 214 can also be coupled to the processing unit 202 through a switched central resource, for example the communication bus 212.

The processing unit 202 can also include a temporary storage 224 and a display controller 226. As an example, the temporary storage 224 can store temporary information. For instance, the temporary storage 224 can be a random access memory.

Example: Classifying Tumors in Locally Advanced Breast Cancer

In this example, tumors were classified based on predictions of tumor response to chemotherapy treatment regimens using the quantitative ultrasound analysis methods described above. The results indicate that the methods are capable of classifying tumor subtypes based on predicted treatment response, thereby providing diagnostic value for evaluating tumors and planning treatment strategies before treating subjects.

Materials and Methods

In this study, ultrasound RF data were collected from the affected breast of 56 patients with locally advanced breast cancer ("LABC") prior to neoadjuvant chemotherapy. Patients in the study were recently diagnosed with locally advanced invasive breast cancer within one week of imaging. Breast cancers included invasive ductal carcinoma, invasive lobular carcinoma, and other forms of invasive cancer, including all grades. This included patients with tumors larger than 5 cm and/or tumors with locoregional lymph node, skin, and chest wall involvement.

Treatment regimens varied from 5-fluorouracil, epirubicin and cyclophosphamide followed by docetaxol (FEC-D), to Adriamycin followed by paclitaxel (AC-T), to taxol followed by herceptin varying from weekly to tri-weekly cycles. A summary of patient characteristics is provided in Table 1, which provides a summary of patient characteristics, with IDC=invasive ductal carcinoma, ILC=Invasive lobular carcinoma, and BTS=bulk tumor shrinkage (percent change in tumor size).

TABLE 1

| Age (y) | 49 ± 10 |
| Pre-tx tumor size (cm) | 6.3 ± 3.2 |

| Tumor subtype | No. | % |
| --- | --- | --- |
| IDC | 52 | 93 |
| ILC | 3 | 5 |
| Other | 1 | 2 |
| Responders | 42 | 75 |
| BTS (%) | 68 ± 47 | |
| Non-responders | 14 | 25 |
| BTS (%) | −16 ± 57 | |

Breast ultrasound data were collected by an experienced breast sonographer with 10 years of experience using a clinical scanner (Sonix RP, Ultrasonix, Vancouver, Canada) employing a 6 MHz linear array transducer (L14-5-60), sampling at a rate of 40 MHz, with the focus set at the midline of the tumor and maximum depth set to 4-6 cm, depending on tumor size and location. Standard B-mode imaging was used for anatomical navigation and acquisition location was determined based on the tumor location reported in biopsy findings. Approximately 3-5 image planes were acquired from the tumor, each 1 cm spaced apart, depending on the tumor size.

The region of interest ("ROI") selection for quantitative ultrasound analysis was performed in a semi-automated manner. First, a 5 mm margin of the tumor was outlined manually from the B-mode breast image, as illustrated in FIG. 3A. Then, an ROI 302 containing the tumor core and an ROI 304 associated with a margin around the core was selected for each patient. In this example, the margin included an approximately 1 cm-wide rim around the tumor core. Otsu's threshold segmentation was applied to the image in FIG. 3A to obtain a binary mask of the core and margin (FIG. 3B). The binary mask was then refined through image dilation in order to obtain a uniform margin with smooth edges (FIG. 3C). The refined binary mask was further refined through hole filling in order to fill holes inside the core (FIG. 3D). This is the final mask that defined the tumor core ROI and the tumor margin ROI for subsequent quantitative ultrasound analyses. As another example, FIG. 4A is a representative conventional ultrasound image (B-mode image) of a patient's breast tumor, and FIG. 4B depicts its corresponding tumor core ROI 402 and tumor margin ROI 404.

The obtained core and margin ROIs were divided into RF blocks for QUS analysis. Each RF block included 20 scan lines each 10 wavelengths long. This approximately corresponded to a 2 mm×2 mm block (assuming a speed of sound of 1540 m/s). Normalized power spectrum was computed for each RF block using a phantom reference, and a parametric image was computed over each tumor ROI for each QUS parameter. The QUS parameters investigated were MBF, SS, SI, ACE, ASD, and AAC. From each parametric map corresponding to core ROI and margin ROI, seven features were computed: mean of intensity, texture features (contrast, correlation, energy, and homogeneity), core-to-margin ratio (CMR), and core-to-margin contrast ratio (CMCR).

Results

Results of response classification using different classifiers are provided in Table 2, which reports the sensitivity, specificity, and accuracy obtained after leave-one-out cross-validation. In each case, a wrapper-based sequential forward feature selection was used to obtain the set of features that yielded the highest classification accuracy, as shown in Table 2.

TABLE 2

| Classifier | Sensitivity (%) | Specificity (%) | Accuracy (%) |
| --- | --- | --- | --- |
| FLD | 79 | 64 | 75 |
| SVM | 90 | 64 | 82 |
| k-NN | 90 | 79 | 88 |

Table 3 presents the classification performance results obtained for different margin thicknesses used to generate $ROI_{margin}$, including 3, 5, and 10 mm thicknesses. Results suggested that 5 mm is the optimal margin thickness for characterizing a patient's tumor responsiveness. The results in Table 3 are based on the classifier that performed the best for each margin thickness, which was the k-NN in all three cases.

TABLE 3

| $ROI_{margin}$ Thickness | Sensitivity (%) | Specificity (%) | Accuracy (%) |
| --- | --- | --- | --- |
| 3 mm | 88 | 41 | 74 |
| 5 mm | 90 | 79 | 88 |
| 10 mm | 85 | 41 | 72 |

The features used in the classification model, and their corresponding level of statistical significance from t-tests, are reported in Table 4. The results in Table 4 indicate the optimal feature set obtained through sequential forward feature selection using the k-NN classifier and a 5 mm thick tumor margin ROI, along with the statistical significance of each parameter. P-values were obtained using an unpaired t-test (one tail, α=0.05) or Mann-Whitney test between the response groups, depending on parameter distribution normality.

TABLE 4

| Parameter | P-value |
|---|---|
| ACE | 0.019 |
| $SI_{margin}^{mean}$ | 0.118 |
| $SI_{core}^{HOM}$ | 0.179 |
| $MBF_{core}^{mean}$ | 0.192 |
| $SI^{CMR}$ | 0.192 |
| $ASD^{CMCR}$ | 0.234 |
| $SS_{core}^{COR}$ | 0.244 |
| $SS^{CMCR}$ | 0.303 |
| $SI^{CMCR}$ | 0.366 |

Results suggest that the statistical and image quality features of spectral parameters may provide more discriminatory information about the response characteristics of a tumor than backscatter model parameters, such as ASD. A Mann-Whitney test on the posterior probabilities of the good response and poor response groups demonstrated highly statistically significant results (p<0.001), further demonstrating the effectiveness of the k-NN based multiparametric classifier in differentiating between the two response groups.

FIGS. 5A-5H displays a panel of images related to one representative good response patient (FIGS. 5A-5D) and one representative poor response patient (FIGS. 5E-5H), including original B-mode images (FIGS. 5A, 5E); parametric images of the best spectral parameter, which was SI (FIGS. 5B, 5F); parametric images of the best backscatter-model-based parameter, which was ASD (FIGS. 5C, 5G); and eosin and hematoxylin (H&E) sections of the post-surgical breast specimen (FIGS. 5D, 5H). The best parameters were determined based on their dominance in the optimal feature set presented in Table 4. As seen in FIGS. 5A and 5E, a tumor in a B-mode image of a LABC patient's breast can be identified as a hypo-intense mass surrounded by a relatively hyper-intense fibroglandular tissue. As seen in FIGS. 5B, 5C, 5F, and 5G, parametric maps of SI and ASD hold further information about the tumor, with each ROI (core and margin) containing a unique textural pattern. The H&E section for the representative good response patient (FIG. 5D) demonstrates only fibroglandular tissue (pink stain) and fibrosis (light pink stain) remaining in the tumor "bed," whereas the H&E section for the poor response patient (FIG. 5H) shows two distinct masses (purple stain) of residual tumor remaining after months of treatment.

Figure 6A:
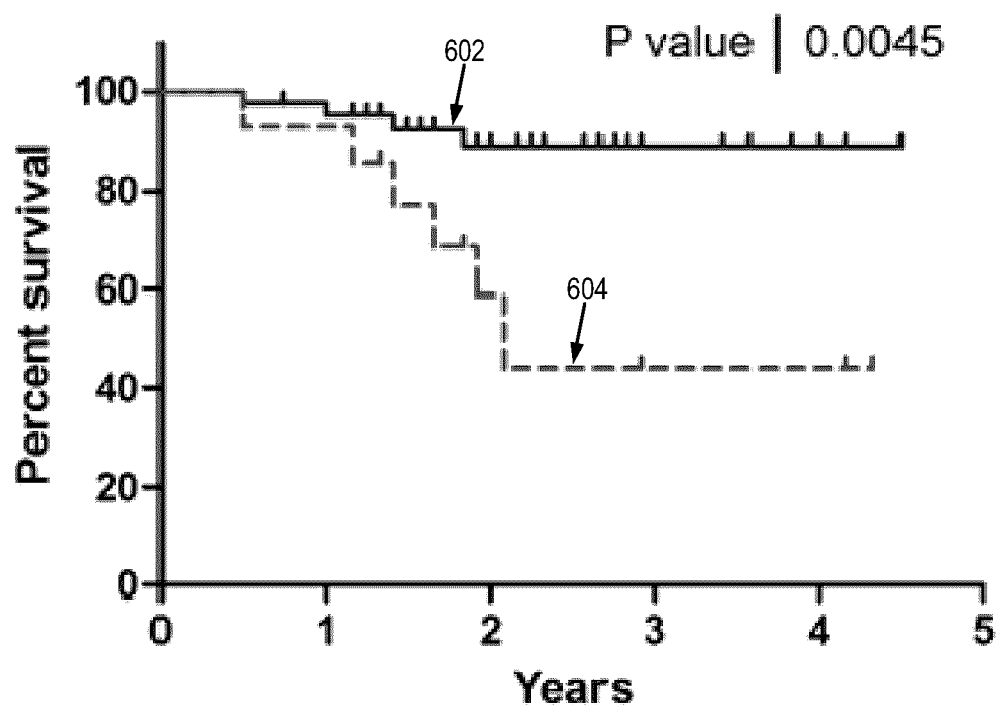
FIGS. 6A and 6B illustrate Kaplan-Meier recurrence-free survival curves based on post-surgical histopathology (FIG. 6A) and the QUS-based analysis methods described here (FIG. 6B).
Figure 6B:
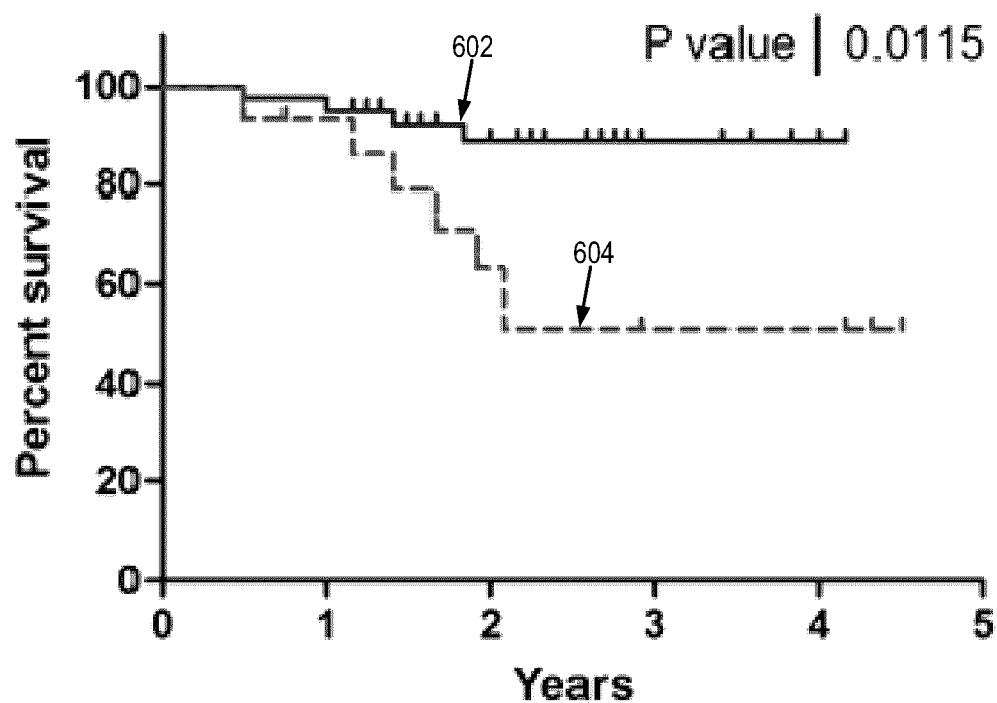

FIGS. 6A and 6B illustrate Kaplan-Meier recurrence-free survival curves based on post-surgical histopathology (FIG. 6A) and the QUS-based analysis methods described here (FIG. 6B). Solid curves 602 represents responders and dashed curves 604 represents non-responders.

The data suggests that the QUS-based analysis methods described above are able to predict the 5-year survival of LABC patients who underwent chemotherapy. The results suggest that ultrasonic features both inside the tumor and in the periphery of the tumor are prognostic factors. To this end, the methods described here can also be used to classify a tumor based on a prognosis for the patient before the patient receives a particular treatment regimen. This prognosis can be based on an estimator, such as progression-free survival time, survival rate, or survival time. The classification of the tumor in this manner can provide additional diagnostic information that can be assessed when making treatment decisions, such as selecting the treatment regimen that is most likely to result in a successful prognosis.

QUS features inside the tumor may reflect tumor features such as cellularity and vascularity, which may describe the aggressiveness of the tumor. Because the SNR/CNR and margin features contributed to the classification of response, it is strongly suggested that the tumor periphery plays an important role in determining tumor aggressiveness and chance of post-surgical recurrence.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for assessing a prediction of tumor response to a chemotherapy treatment using an ultrasound system, the steps of the method comprising:
   (a) acquiring ultrasound echo signal data from a subject using the ultrasound system;
   (b) providing an anatomical image of the subject;
   (c) identifying in the anatomical image a region-of-interest (ROI) that contains a tumor;
   (d) generating at least one parametric map from the ultrasound echo signal data, the at least one parametric map having pixel values associated with a parameter computed from the acquired ultrasound echo signal data acquired from the ROI;
   (e) computing at least one of a first-order statistical measure, a second-order statistical measure, or an image quality measure based on the at least one parametric map; and
   classifying the tumor by applying a classifier to the computed at least one first-order statistical measure, second-order statistical measure, or image quality measure, wherein classifying the tumor indicates a prediction of the tumor's response to a chemotherapy treatment;
   wherein:
      step (e) includes computing both a first-order statistical measure and a second-order statistical measure based on the at least one parametric map; and
      step (f) includes classifying the tumor by applying the classifier to both the computed first-order statistical measure and second-order statistical measure.

2. The method as recited in claim 1, wherein the ROI includes a region associated with a core of the tumor and a region associated with a margin around the core.

3. The method as recited in claim 2, wherein step (e) includes computing at least one of a first-order statistical measure or a second-order statistical measure for each region in the ROI.

4. The method as recited in claim 2, wherein step (e) includes computing at least one of a signal-to-noise ratio (SNR) or a contrast-to-noise ratio (CNR) based on both regions in the ROI.

5. The method as recited in claim 1, wherein the at least one parametric map has pixel values associated with a parameter that includes at least one of mid-band fit, spectral slope, spectral 0-MHz intercept, attenuation coefficient estimate, average scatterer diameter, and average acoustic concentration.

6. The method as recited in claim 1, wherein the first-order statistical measure is at least one of a mean, a standard deviation, a skewness, and a kurtosis.

7. The method as recited in claim 1, wherein the second-order statistical measure is at least one of contrast, energy, homogeneity, correlation, autocorrelation, dissimilarity, gray-level co-occurrence matrix variability, entropy, cluster shade, cluster prominence, and maximum probability.

8. The method as recited in claim 1, wherein step (d) includes computing a normalized power spectrum of the ultrasound echo signal data acquired from the ROI and producing the at least one parametric map by computing the parameter from the normalized power spectrum.

9. The method as recited in claim 8, wherein step (d) includes providing reference echo signal data obtained from a phantom using the ultrasound system and computing the normalized power spectrum using the provided reference echo signal data such that effects from the ultrasound system are minimized in the normalized power spectrum.

10. The method as recited in claim 1, wherein the classifier is at least one of a Fisher's linear discriminant classifier, a support vector machine classifier, or a k-nearest neighbors classifier.

11. The method as recited in claim 1, wherein step (b) includes acquiring a B-mode image of the subject using the ultrasound system.

12. A computer-implemented method for using an ultrasound system to assess a prognosis for a subject who will be treated with a particular tumor treatment regimen, the steps of the method comprising:
 (a) acquiring ultrasound echo signal data from a subject using the ultrasound system;
 (b) providing an anatomical image of the subject;
 (c) identifying in the anatomical image a region-of-interest (ROI) that contains a tumor;
 (d) generating at least one parametric map from the ultrasound echo signal data, the at least one parametric map having pixel values associated with a parameter computed from the acquired ultrasound echo signal data acquired from the ROI;
 (e) computing at least one of a first-order statistical measure, a second-order statistical measure, or an image quality measure based on the at least one parametric map; and
 classifying the tumor by applying a classifier to the computed at least one first-order statistical measure, second-order statistical measure, or image quality measure, wherein classifying the tumor indicates a prognosis for the subject following treatment with a particular tumor treatment regimen;
 wherein:
  step (e) includes computing both a first-order statistical measure and a second-order statistical measure based on the at least one parametric map; and
  step (f) includes classifying the tumor by applying the classifier to both the computed first-order statistical measure and second-order statistical measure.

13. The method as recited in claim 12, wherein the prognosis for the subject is based on an estimator selected from the group consisting of a progression-free survival, a survival rate, and a survival time.

14. The method as recited in claim 12, wherein the ROI includes a region associated with a core of the tumor and a region associated with a margin around the core.

15. The method as recited in claim 14, wherein step (e) includes computing at least one of a first-order statistical measure or a second-order statistical measure for each region in the ROI.

16. The method as recited in claim 14, wherein step (e) includes computing at least one of a signal-to-noise ratio (SNR) or a contrast-to-noise ratio (CNR) based on both regions in the ROI.

17. The method as recited in claim 12, wherein the at least one parametric map has pixel values associated with a parameter that includes at least one of mid-band fit, spectral slope, spectral 0-MHz intercept, attenuation coefficient estimate, average scatterer diameter, and average acoustic concentration.

18. The method as recited in claim 12, wherein the first-order statistical measure is at least one of a mean, a standard deviation, a skewness, and a kurtosis.

19. The method as recited in claim 12, wherein the second-order statistical measure is at least one of contrast, energy, homogeneity, correlation, autocorrelation, dissimilarity, gray-level co-occurrence matrix variability, entropy, cluster shade, cluster prominence, and maximum probability.

20. The method as recited in claim 12, wherein step (d) includes computing a normalized power spectrum of the ultrasound echo signal data acquired from the ROI and producing the at least one parametric map by computing the parameter from the normalized power spectrum.

21. The method as recited in claim 20, wherein step (d) includes providing reference echo signal data obtained from a phantom using the ultrasound system and computing the normalized power spectrum using the provided reference echo signal data such that effects from the ultrasound system are minimized in the normalized power spectrum.

22. The method as recited in claim 12, wherein the classifier is at least one of a Fisher's linear discriminant classifier, a support vector machine classifier, or a k-nearest neighbors classifier.

23. The method as recited in claim 12, wherein step (b) includes acquiring a B-mode image of the subject using the ultrasound system.

* * * * *

UNITED STATES PATENT AND TRADEMARK OFFICE
CERTIFICATE OF CORRECTION

PATENT NO. : 11,049,238 B2
APPLICATION NO. : 15/739003
DATED : June 29, 2021
INVENTOR(S) : Hadi Tadayyon et al.

Page 1 of 1

It is certified that error appears in the above-identified patent and that said Letters Patent is hereby corrected as shown below:

In the Claims

Claim 1, Column 12, Line 33: "classifying the tumor by..." should be "(f) classifying the tumor by..."
Claim 12, Column 13, Line 40: "classifying the tumor by..." should be "(f) classifying the tumor by..."

Signed and Sealed this
Twenty-second Day of March, 2022

Drew Hirshfeld
*Performing the Functions and Duties of the
Under Secretary of Commerce for Intellectual Property and
Director of the United States Patent and Trademark Office*